United States Patent [19]

Forbes et al.

[11] Patent Number: 5,328,922
[45] Date of Patent: Jul. 12, 1994

[54] INDOLE UREAS AS 5 HT RECEPTOR ANTAGONIST

[75] Inventors: Ian T. Forbes; Roger T. Martin, both of Harlow, Great Britain

[73] Assignee: Beecham Group p.l.c., United Kingdom

[21] Appl. No.: 30,103

[22] PCT Filed: Sep. 11, 1991

[86] PCT No.: PCT/GB91/01553

§ 371 Date: May 11, 1993

§ 102(e) Date: May 11, 1993

[87] PCT Pub. No.: WO92/05170

PCT Pub. Date: Apr. 2, 1992

[30] Foreign Application Priority Data

Sep. 13, 1990 [GB] United Kingdom ............... 9020030
Mar. 22, 1991 [GB] United Kingdom ............... 9106079
Mar. 22, 1991 [GB] United Kingdom ............... 9106092
Mar. 22, 1991 [GB] United Kingdom ............... 9106094

[51] Int. Cl.$^5$ .................... A61K 31/44; C07D 401/12

[52] U.S. Cl. .................... 514/339; 546/273; 546/309

[58] Field of Search .................... 546/273; 514/339

[56] References Cited

U.S. PATENT DOCUMENTS 4,273,782  6/1981  Cross et al. .................... 514/399
4,346,093  8/1982  Friebe et al. .................... 548/259 X

OTHER PUBLICATIONS

P. Fludinski et al., *J. Med. Chem.*, 1986, 29, 2415.

*Primary Examiner*—Alan L. Rotman
*Attorney, Agent, or Firm*—Linda E. Hall; Stuart R. Suter; Edward T. Lentz

[57] ABSTRACT

A class of compounds identified as N-(1-methyl-1H-indol-5-yl)-(2,3 or 4-pyridyl)ureas, derivatives thereof, methods for their preparation, pharmaceutical compositions containing same and their 5-HT receptor antagonist activity are believed to be of potential use in the treatment of a variety of CNS disorders are described herein.

8 Claims, No Drawings

INDOLE UREAS AS 5 HT RECEPTOR ANTAGONIST

This invention relates to compounds having pharmacological activity, to a process for their preparation, to compositions containing them and to their use in the treatment of mammals.

P. Fludzinski et. al., J. Med. Chem. 1986 29 2415-2418 describes N-(1,2-dimethyl-3-ethyl-1H-indol-5-yl)-N'-(3-trifluoromethylphenyl)urea which shows selectivity for the rat stomach fundus serotonin receptor.

A class of compounds has now been discovered, which compounds have been found to have $5HT_{1C}$ receptor antagonist activity. $5HT_{1C}$ receptor antagonists are believed to be of potential use in the treatment of CNS disorders such as anxiety, depression, obsessive compulsive disorders, migraine, anorexia, Alzheimers disease, sleep disorders, bulimia, panic attacks, withdrawal from drug abuse and/or schizophrenia.

Accordingly, the present invention provides a compound of formula (I) or a pharmaceutically acceptable salt thereof:

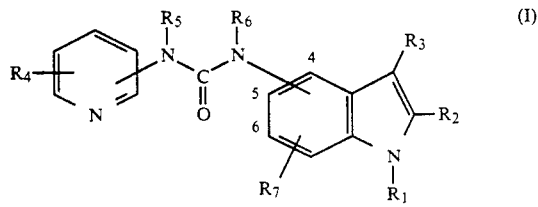

wherein:

$R_1$, $R_2$ and $R_3$ are independently hydrogen or $C_{1-6}$ alkyl;

$R_4$ is hydrogen, $C_{1-6}$ alkyl, halogen, hydroxy or $NR_8R_9$ where $R_8$ and $R_9$ are independently hydrogen or $C_{1-6}$ alkyl;

$R_5$ and $R_6$ are independently hydrogen or $C_{1-6}$ alkyl; and $R_7$ is hydrogen, $C_{1-6}$ alkyl or halogen; and wherein the urea moiety is attached at the 4-, 5- or 6-position of the indole ring.

Alkyl moieties within the variables $R_1$ to $R_9$ are preferably $C_{1-3}$ alkyl, such as methyl, ethyl, n- and iso-propyl, most preferably methyl, ethyl and n-propyl.

Suitable $R_4$ and $R_7$ halogens include chloro and bromo.

Examples of $R_1$ include hydrogen, methyl, ethyl and n-propyl, preferably methyl. $R_2$ is preferably methyl or hydrogen and $R_3$ is hydrogen, methyl, ethyl, n-propyl, iso-propyl or n-hexyl.

Preferably $R_4$ is hydrogen, chloro, hydroxy or dimethylamino, most preferably hydrogen.

Preferably $R_5$, $R_6$ and $R_7$ are independently hydrogen or methyl.

The urea moiety may be attached at the 2-, 3-, 4-, 5- or 6-position of the pyridine ring, preferably the 3-, 4- or 5-position.

The urea moiety is preferably attached at the 4- or 5-position of the indole ring.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form solvates such as hydrates, and the invention also extends to these forms. When referred to herein, it is understood that the term 'compound of formula (I)' also includes solvates thereof. When $R_5$ and/or $R_6$ are hydrogen or when $R_4$ is 2- or 4-hydroxy or $NR_8R_9$ and at least one of $R_8$ and $R_9$ are hydrogen the compounds of formula (I) may exist tautomerically in more than one form. The invention extends to each of these forms and mixtures thereof.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis.

The present invention also provides a process for the preparation of a compound of formula (I) or a pharmaceutically acceptable salt thereof, which process comprises (a) the coupling of a compound of formula (II);

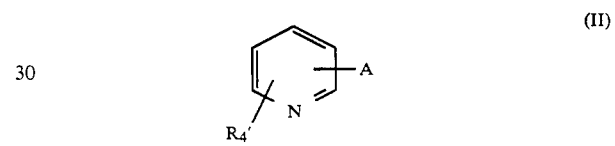

with a compound of formula (III);

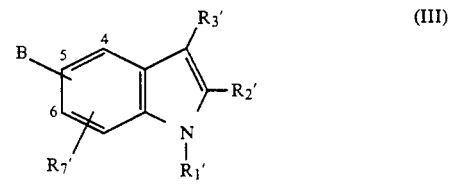

wherein B is attached at the 4-, 5- or 6-position of the indole ring and A and B contain the appropriate functional group(s) necessary to form the moiety —$NR_5$'$CONR_6$'- when coupled, wherein $R_5$' and $R_6$' are $R_5$ and $R_6$ as defined in formula (I) or groups convertible thereto, and the variables $R_1$', $R_2$', $R_3$', $R_4$' and $R_7$' are $R_1$, $R_2$, $R_3$, $R_4$ and $R_7$ respectively, as defined in formula (I), or groups convertible thereto, and thereafter optionally and as necessary and in any appropriate order, converting any $R_1$', $R_2$', $R_3$', $R_4$', $R_5$', $R_6$' and $R_7$' when other than $R_1$, $R_2$, $R_3$, $R_4$, $R_5$, $R_6$ and $R_7$ respectively to $R_1$, $R_2$, $R_3$, $R_4$, $R_5$, $R_6$ and $R_7$, interconverting $R_1$, $R_2$, $R_3$, $R_4$, $R_5$, $R_6$ and $R_7$, and forming a pharmaceutically acceptable salt thereof, or (b) cyclising a compound of formula (IV):

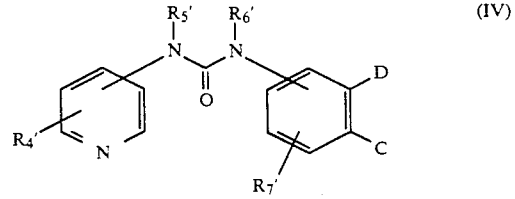

wherein $R_4'$, $R_5'$, $R_6'$ and $R_7'$ are as defined in formulae (II) and (III) and C and D contain the appropriate functional group(s) necessary to form the indole ring substituted by $R_1'$, $R_2'$ and $R_3'$ as defined in formula (III), and thereafter optionally and as necessary in any appropriate order, converting any $R_1'$, $R_2'$, $R_3'$, $R_4'$, $R_5'$, $R_6'$ and $R_7'$ when other than $R_1$, $R_2$, $R_3$, $R_4$, $R_5$, $R_6$ and $R_7$, to $R_1$, $R_2$, $R_3$, $R_4$, $R_5$, $R_6$ and $R_7$, interconverting $R_1$, $R_2$, $R_3$, $R_4$, $R_5$, $R_6$ and $R_7$ and forming a pharmaceutically acceptable salt.

Suitable examples of groups A and B are
(i) A is —N=C=O and B is —NHR$_6'$,
(ii) A is —NHR$_5'$ and B is —N=C=O,
(iii) A is —NR$_5'$COL and B is —NHR$_6'$,
(iv) A is —NHR$_5'$ and B is —NR$_6'$COL, or
(v) A is halogen and B is —NR$_6'$CONHR$_5'$,
wherein R$_5'$ and R$_6'$ are as defined above and L is a leaving group. Examples of suitable leaving groups L include halogen such as chloro or bromo, imidazole, or phenoxy or phenylthio optionally substituted for example with halogen.

When A is —N=C=O and B is NHR$_6'$ or when A is NHR$_5'$ and B is —N=C=O the reaction is suitably carried out in an inert solvent for example dichloromethane or toluene at ambient temperature.

When A is —NR$_5'$COL and B is —NHR$_6'$ or when A is —NHR$_5'$ and B is —NR$_6'$COL, the reaction is suitably carried out in an inert solvent such as dichloromethane at ambient temperature optionally in the presence of a base, such as triethylamine or in dimethylformamide at ambient or elevated temperature.

When A is halogen and B is —NR$_6'$CONHR$_5'$, the reaction is suitably carried out in an inert solvent such as toluene at elevated temperature, optionally in the presence of a base.

The cyclisation of the compound of formula (IV) may be effected using standard methodology such as described in Comprehensive Heterocyclic Chemistry 1984 4, 313 et. seq. or J. Het. Chem. 1988 25 p.1 et seq.

Examples of the more important routes include the Leimgruber synthesis, the Fischer synthesis and the Japp-Klingemann variation and the Madelung synthesis.

Examples of the groups C and D thus include
(vi) C=NO$_2$ and D=CH=CH—NZ$_2$ where each Z is independently $C_{1-6}$ alkyl or together represent $C_{2-7}$ alkylene;
(vii) C=NR$_1'$—N=C(R$_2'$)—CH$_2$R$_3'$ and D=H;
(viii) C=NH—N=C(CO$_2$X)—CH$_2$R$_3'$ and D=H where X is $C_{1-6}$ alkyl; and
(ix) C=NR$_1'$COR$_2'$ and D=CH$_2$R$_3'$.

In reaction variant (vi) (Leimgruber synthesis) the compound of formula (IV) is prepared from the 2-methylnitrophenyl urea by treatment with a dialkylacetal of the dialkylformamide OHCNZ$_2$ with heating and the product of formula (IV) cyclised by hydrogenation over a suitable catalyst such as palladium and charcoal optionally under pressure to yield the compound of formula (I) where $R_1=R_2=R_3=H$.

In reaction variant (vii) (Fischer synthesis) the compound of formula (IV) is prepared from the hydrazinophenyl urea by dehydration, preferably by heating, with the appropriate ketone R$_2'$COCH$_2$R$_3'$ and the product of formula (IV) cyclised by heating with an acid catalyst such as hydrochloric or sulphuric acid.

In reaction variant (viii) (Japp-Klingemann synthesis) the compound of formula (IV) is prepared from the aminophenyl urea by diazotisation followed by treatment for example with CH$_3$COCH(CO$_2$X)—CH$_2$R$_3'$ where X is $C_{1-6}$ alkyl under basic conditions in aqueous alcohol as solvent.

The product of formula (IV) may then be cyclised as in the Fischer synthesis above.

In reaction variant (ix) (Madelung synthesis) the compound of formula (IV) is cyclised with base in an inert solvent optionally with heating.

Suitable examples of groups R$_2'$, R$_3'$, R$_4'$, and R$_7'$ which are convertible to R$_2$, R$_3$, R$_4$, and R$_7$ respectively, include acyl groups which are introduced conventionally and may be converted to the corresponding alkyl group by conventional reduction, such as using sodium borohydride in an inert solvent followed by hydrogenolysis in an inert solvent and alkoxycarbonyl groups which may be converted to hydrogen by hydrolysis and decarboxylation. When R$_4$ is hydroxy it is preferably protected in the compound of formula (II) as, for example, an aryloxy group such as benzyloxy which is removed by hydrogenation.

Suitable examples of a group R$_1'$ which is convertible to R$_1$, include typical N-protecting groups such as alkoxycarbonyl, in particular t-butyloxycarbonyl, acetyl, trifluoroacetyl, benzyl and para-methoxybenzyl which are converted to R$_1$ hydrogen using conventional conditions.

Suitable examples of groups R$_5'$ and R$_6'$ which are convertible to R$_5$ and R$_6$ respectively include alkoxycarbonyl and benzyl or para-methoxybenzyl which are converted to R$_5$ and/or R$_6$ hydrogen using conventional conditions.

Interconversions of R$_1$, R$_2$, R$_3$, R$_4$, R$_5$, R$_6$ and R$_7$ are carried out by conventional procedures. For example, in the case wherein R$_1$, R$_2$ and R$_3$ are $C_{1-6}$ alkyl and R$_5$ and R$_6$ are hydrogen it is possible to introduce a $C_{1-6}$ alkyl group at both the R$_5$ and R$_6$ positions by conventional alkylation using 2 molar equivalents of a $C_{1-6}$ alkyl halide and 2 molar equivalents of a suitable base in an inert solvent. Monoalkylation can be achieved using 1 molar equivalent of a $C_{1-6}$ alkyl halide and base using conventional conditions. R$_1$ $C_{1-6}$ alkyl groups may also be introduced by conventional alkylation, for example using a $C_{1-6}$ alkyl halide and base such as sodium hydride.

R$_4$ halo and R$_7$ halo may be introduced by selective halogenation of the pyridine ring or indole ring respectively using conventional conditions.

It should be appreciated that it may be necessary to protect any R$_1$ to R$_7$ hydrogen variables which are not required to be interconverted.

Suitable protecting groups and methods for their attachment and removal are conventional in the art of organic chemistry, such as those described in Greene T. W. 'Protective groups in organic synthesis' New York, Wiley (1981).

It is preferable, however, to introduce and interconvert the groups R$_1$ to R$_7$ before coupling compounds of formulae (II) and (III) together, or cyclising the compound of formula (IV).

Compounds of formula (II) in which A is NHR$_5'$ are known compounds or can be prepared analogously to known compounds. For example, the compounds of formula (II) in which A is 3-amino and R$_4'$ is hydrogen, 2-chloro or 6-chloro, and A is 2-amino and R$_4'$ is 3-benzyloxy are commercially available from the Aldrich Chemical Company in the UK. R$_5'$ $C_{1-6}$ alkyl groups may be introduced conventionally, for example by reductive alkylation or acylation and reduction.

Compounds of formula (II) in which A is —N=C=O may be prepared by treating a compound of formula (II) in which:

i) A is amino, with phosgene or a phosgene equivalent, in the presence of excess base in an inert solvent.

ii) A is acylazide (i.e. $CON_3$), via the nitrene, by thermal rearrangement using conventional conditions (ref L. S. Trifonov et al, Helv. Chim. Acta 1987 70 262).

iii) A is $CONH_2$, via the nitrene intermediate using conventional conditions.

Compounds of formula (II) in which A is —$NR_5$'COL may be prepared by reacting a compound of formula (II) in which A is —$NHR_5$' with phosgene or a phosgene equivalent, in an inert solvent, at low temperature, if necessary in the presence of one equivalent of a base such as triethylamine.

Compounds of formula (II) in which A is halogen and $R_4$' is hydrogen are commercially available.

Compounds of formula (III) in which B is $NHR_6$' are known compounds or can be prepared analogously to known compounds, for example by reduction of the corresponding nitroindole by catalytic hydrogenation over Pd/C by the method of P. Fludzinski et al J. Med. Chem., 1986, 29 2415. Specifically, the compound of formula (III) in which $R_1$' and $R_2$' are methyl, $R_3$' is ethyl, $R_6$' and $R_7$' are hydrogen and B is $NH_2$ is prepared using a procedure similar to that described by Fludzinski.

The nitroindoles are commercially available, for example 5-nitroindole, or may be prepared conventionally (Comprehensive Heterocyclic Chemistry Vol. 4 p. 313 et. seq. (Pergamon Press 1984) and J. Her. Chem. 1988 25 p.1 et. seq.)

An $R_2$' alkoxycarbonyl group may be eliminated to give $R_2$' hydrogen, generally under the conditions effecting formation of the nitroindole or as a subsequent step in the process.

$R_6$' alkyl groups may be introduced conventionally, for example by reductive alkylation or acylation and reduction. $R_7$' $C_{1-6}$ alkyl groups may be introduced ortho to a nitro substituent by alkylation using a procedure similar to that described in G. Bartoli et. al., J. Org. Chem. 1986 51 3694 and Tetrahedron 1987 43 4221.

Compounds of formula (III) in which B is —N=C=O may be prepared by treating a compound of formula (III) in which:

i) B is amino, with phosgene or a phosgene equivalent, in the presence of excess base in an inert solvent.

ii) B is acylazide (i.e. $CON_3$), via the nitrene, by thermal rearrangement using conventional conditions.

iii) B is $CONH_2$, via the nitrene intermediate using conventional conditions.

Compounds of formula (III) in which B is —$NR_6$'COL may be prepared by reacting a compound of formula (III) in which B is —$NHR_6$' with phosgene or a phosgene equivalent, in an inert solvent, at low temperature, if necessary in the presence of one equivalent of a base such as triethylamine.

Compounds of formula (III) in which B is —$NR_6$'CONHR$_5$' can be prepared from the corresponding precursor where B is $NHR_6$' by reaction with an $R_5$' isocyanate under conventional conditions.

Examples of phosgene equivalents include triphosgene, carbonyldiimidazole, phenyl chloroformate and phenyl chlorothioformate.

Novel intermediates of formula (III) also form part of the invention.

Compounds of formula (IV) may be prepared from the appropriate aminophenyl derivative analogously to compounds of formula (I). Intermediates of formula (IV) also form part of the invention.

Pharmaceutically acceptable salts may be prepared conventionally by reaction with the appropriate acid or acid derivative.

Compounds of formula (I) and their pharmaceutically acceptable salts have $5HT_{1C}$ receptor antagonist activity and are believed to be of potential use in the treatment or prophylaxis of anxiety, depression, migraine, anorexia, obsessive compulsive disorders, Alzheimer's disease, sleep disorders, bulimia, panic attacks, withdrawal from drug abuse and/or schizophrenia. Thus the invention also provides a compound of formula (I) or a pharmaceutically acceptable salt thereof, for use as a therapeutic substance, in particular in the treatment or prophylaxis of anxiety, depression, migraine, anorexia, obsessive compulsive disorders, Alzheimer's disease, sleep disorders, bulimia, panic attacks, withdrawal from drug abuse and/or schizophrenia.

The invention further provides a method of treatment or prophylaxis of anxiety, depression, migraine, anorexia, obsessive compulsive disorders, Alzheimer's disease, sleep disorders, bulimia, panic attacks, withdrawal from drug abuse and/or schizophrenia in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of anxiety, depression, migraine, anorexia, obsessive compulsive disorders, Alzheimer's disease, sleep disorders, bulimia, panic attacks, withdrawal from drug abuse and/or schizophrenia.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.01 to 100 mg/kg; and such therapy may extend for a number of weeks or months.

When administered in accordance with the invention, no unacceptable toxicological effects are expected with the compounds of the invention.

The following Examples illustrate the preparation of pharmacologically active compounds of the invention. The following Descriptions illustrate the preparation of intermediates to compounds of the present invention.

DESCRIPTION 1

5-Amino-1,2-dimethyl-3-ethyl-1H-indole (D1)

The title compound was prepared using a procedure similar to that described by P. Fludzinski et al in J. Med. Chem., 1986, 29,2415.

DESCRIPTION 2

1-Methyl-5-nitro-1H-indole (D2)

To a stirred suspension of sodium hydride (5.0 g; 167 mM) in dimethylformamide (200 ml) at 0° C. under nitrogen was added 5-nitroindole (25 g; 154 mM) in dimethylformamide. After stirring for 0.5 h, iodomethane (10.5 ml; 168 mM) in dimethylformamide (50 ml) was added, and stirring was continued for 2 h. The reaction mixture was then quenched with water, and poured onto excess water with stirring. Filtration afforded the title compound (27.4 g; 94%).

NMR (CDCl$_3$) δ: 3.88 (3H, s), 6.68 (1H, d, J=3) 7.21 (1H, d, J=3) 7.34 (1H, d, J=8) 8.13 (1H, dd, J=8, 2) 8.59 (1H, d, J=2).

DESCRIPTION 3

5-Amino-1-methyl-1H-indole (D3)

A mixture of the nitroindole (D2) (5 g; 28.4 mM) and 5% palladium on charcoal in ethanol (300 ml) was hydrogenated at 60 p.s.i. (4.14×10$^5$ Pa) at room temperature for 3 h. Removal of the catalyst by filtration followed by evaporation of the solvent gave the title compound (3.39 g; 95%).

NMR (CDCl$_3$) δ: 3.20 (2H, broad s), 3.70 (3H, s), 6.28 (1H, d, J=3) 6.68 (1H, dd, J=8, 2), 6.92 (1H, d, J=2), 6.96 (1H, d, J=3), 7.12 (1H, d, J=8).

DESCRIPTION 4

3-Pyridyl isocyanate (D4)

The title compound was prepared from 3-pyridinecarbonyl azide in toluene using a procedure similar to that described by L. S. Trifonov et al in Helv. Chim. Acta, 1987, 70, 262.

DESCRIPTION 5

5-Nitro-1,2, 3-trimethyl-1H-indole (D5)

The title compound was prepared in 99% yield from 2,3-dimethyl-5-nitroindole using a procedure similar to that in Description 2.

NMR (CDCl$_3$) δ: 2.28 (3H, s), 2.38 (3H, s), 3.71 (3H, s), 7.22 (1H, d, J=8), 8.06 (1H, dd, J=8, 2), 8.46 (1H, d, J=2).

DESCRIPTION 6

5-Amino-1,2,3-trimethyl-1H-indole (D6)

The title compound was prepared in 91% yield from the nitroindole (D5) using a procedure similar to that in Description 3.

NMR (CDCl$_3$) δ: 2.18 (3H, s), 2.29 (3H, s), 3.00 (2H broad s), 3.57 (3H, s), 6.60 (1H, dd, J=8, 2) 6.80 (1H, d, J=2), 7.03 (1H, d, J=8).

DESCRIPTION 7

5-Nitro-1-propyl-1H-indole (D7)

The title compound was prepared in 96% yield from 5-nitroindole and propyl iodide using a procedure similar to that in Description 2.

NMR (CDCl$_3$) δ: 0.96 (3H, t, J=7), 1.90 (2H, h, J=7), 4.13 (2H, t, J=7), 6.68 (1H, d, J=3), 7.26 (1H, d, J=3), 7.37 (1H, d, J=8), 8.10 (1H, dd, J=8, 2), 8.59 (1H, d, J=2).

DESCRIPTION 8

5-Amino-1-propyl-1H-indole (D8)

The title compound was prepared in 100% yield from the nitroindole (D7) using a procedure similar to that in Description 3.

NMR (CDCl$_3$) δ: 0.91 (3H, t, J=7, 1.83 (2H, h, J=7), 3.38 (2H, broad s), 4.02 (2H, t, J=7), 6.29 (1H, d, J=3), 6.68 (1H, dd, J=8, 2), 6.93 (1H, d, J=2), 7.01 (1H, d, J=3), 7.14 (1H, d, J=8).

DESCRIPTION 9

1-Methyl-4-nitro-1H-indole (D9)

To a stirred suspension of sodium hydride (0.14 g; 3.41 mM) in dimethylformamide (10 ml) at 0° C. under nitrogen was added 4-nitroindole (0.5 g; 3.1 mM) in dimethylformamide. After stirring for 0.5 h, iodomethane (0.21 ml; 3.41 mM) in dimethylformamide (1 ml) was added, and stirring was continued for 1 h. The reaction mixture was then quenched with water, and poured onto excess water with stirring. Filtration afforded the title compound (0.5 g; 92%).

NMR (CDCl$_3$) δ: 3.89 (3H, s), 7.30 (3H, m), 7.66 (1H, d, J=8), 8.15 (1H, d, J=8).

DESCRIPTION 10

4-Amino-1-methyl-1H-indole (D10)

A mixture of the nitroindole (D9) (0.5 g; 2.8 mM) and 5% palladium on charcoal in ethanol (75 ml) was hydrogenated at 60 p.s.i. (4.14×10$^5$ Pa) at room temperature for 2 h. Removal of the catalyst by filtration followed by evaporation of the solvent gave the title compound (0.44 g; 97%).

NMR (CDCl$_3$) δ: 3.76 (3H, s), 6.42 (1H, d, J=2), 6.45 (1H, d, J=8), 6.81 (1H, d, J=8), 6.96 (1H, d, J=2), 7.05 (1H, t, J=8).

DESCRIPTION 11

1-Methyl-6-nitro-1H-indole (D11)

To a solution of sodium hydride (0.27 g; 6.8 mM) in dimethylformamide (4 ml) at 0° C. under nitrogen, was added 6-nitroindole (1 g; 6.2 mM) in dimethylformamide (12 ml). After stirring at room temperature for 0.5 h, iodomethane (0.42 ml; 6.8 mM) in dimethylformamide (1 ml) was added and stirring continued for 1 h. The reaction mixture was then quenched with water, and poured onto excess water with stirring. Filtration afforded the title compound (1.03 g; 94%).

NMR (CDCl$_3$) δ: 3.60 (3H, s), 6.60 (1H, d, J=4), 7.35 (1H, d, J=4), 7.55 (1H, d, J=10), 8.10 (1H, dd, J=10, 2), 8.34 (1H, d, J=2).

DESCRIPTION 12

6-Amino-1-methyl-1H-indole (D12)

A mixture of the nitroindole (D11) (0.8 g; 4.55 mM) and 5% palladium on charcoal in ethanol (150 ml) was hydrogenated at 60 p.s.i. (4.14×10$^5$ Pa) at room temperature for 2 h. Removal of the catalyst by filtration followed by evaporation of the solvent gave the crude product.

Chromatography on silica using dichloromethane as eluant afforded the title compound (0.3 g; 45%).

NMR (CDCl$_3$) δ: 3.68 (3H, s), 6.38 (1H, d, J=3), 6.55-6.65 (2H, m), 6.88 (1H, d, J=3), 7.40 (1H, s, J=10).

DESCRIPTION D13

3-Methylaminopyridine (D13)

A mixture of 3-aminopyridine (5.76 g; 60 mM) in triethylorthoformate (49 ml) was refluxed with stirring for 5 h. The excess solvent was removed in vacuo to give an oil (8.53 g, 93%). The oil was dissolved in ethanol (30 ml) and cooled in ice. To this solution was added sodium borohydride (2.58 g, 68.3 mM) portionwise and left to stir at room temperature for 17 h. The solution was cooled in an ice bath, and water added slowly (3 ml), followed by 5N HCl until no further evolution of gas was observed. The pH was adjusted to 7, then extracted using ethyl acetate, washed with water, dried and evaporated to give an oil (5.10 g; 83%). Chromatography on silica using dichloromethane as eluant afforded the title compound (1.43 g; 22%).

NMR (CDCl$_{13}$) δ: 2.82 (3H, s), 4.12 (1H, s), 6.87 (1H, dd, J=8, 3), 7.09 (1H, m), 7.95 (1H, dd, J=3, 1), 8.02 (1H, d, J=3).

DESCRIPTION 14

N-(1-Methyl-1H-indol-5-yl)formamide (D14)

To acetic anhydride (1.68 ml; 15 mM) at 0° C. was added 98% formic acid (0.8 ml; 21 mM) dropwise under a nitrogen atmosphere, to generate acetic formic anhydride. The solution was heated at 50°-60° C. for 2 h then cooled to room temperature. Dichloromethane (2 ml) was added and the solution was cooled to −20° C. before adding a solution of aminoindole (D3) (1 g, 6.88 mM) in dichloromethane (4 ml). The mixture was stirred at room temperature for 17 h then evaporated to dryness to give a brown oil (1.34 g) Chromatography on silica using ethyl acetate as eluant afforded the title compound (1.05 g; 88%).

NMR (CDCl$_3$) δ: Complex spectrum due to amide isomers.

Found: M+ 174

$C_{10}H_{10}N_2O$ requires 174.

DESCRIPTION 15

1-Methyl-5-methylamino-1H-indole (D15)

To a suspension of lithium aluminium hydride (0.33 g; 8.7 mM) in dry tetrahydrofuran (15 ml) at 0° C. under a nitrogen atmosphere was added the amide (D14) (1.0 g; 5.74 mM). The solution was left to stir at room temperature for 17 h, cooled to 0° C. and then water (3.5 ml), 5 N sodium hydroxide solution (3.5 ml) and then water (5 ml) added in that order. The solution was left to stir for 10 min, then filtered and evaporated to give a brown oil (0.89 g). Chromatography on silica using dichloromethane as eluant gave the title compound (0.57 g; 62%).

NMR (CDCl$_3$) δ: 2.9 (3H, s), 3.52 (1H, s), 3.73 (3H, s), 6.33 (1H, d, J=3), 6.69 (1H, dd, J=8, 1), 6.87 (1H, d, J=1), 6.97 (1H, d, J=3), 7.16 (1H, d, J=8).

DESCRIPTION 16

1,4-Dimethyl-5-nitroindole (D16)

The title compound was prepared from 1-methyl-5-nitroindole (D2) using a procedure similar to that described by G. Bartoli et al in J. Org. Chem. 1986, 51, 3694 and Tetrahedron 1987, 43, 4221. This gave a yellow solid, m.p. 120°-3° C., in 64% yield.

NMR (CDCl$_3$) 2.84 (3H, s), 3.83 (3H, s), 6.71 (1H, d, J=3), 7.18 (1H, d, J=3), 7.20 (1H, d, J=8), 7.99 (1H, d, J=8).

Found: M+ 190

$C_{10}H_{10}N_2O_2$ requires 190.

Found: C, 63.0; H, 5.3; N, 14.6%. $C_{10}H_{10}N_2O_2$ requires C, 63.1; H, 5.3; N, 14.7%.

DESCRIPTION 17

5-Amino-1,4-dimethylindole (D17)

The title compound was prepared from 1,4-dimethyl-5-nitroindole (D16) by catalytic hydrogenation as described in Description 3. This gave a dark purple oil in 92% yield.

NMR (CDCl$_3$) δ: 2.34 (3H, S), 3.1 (2H, bs), 3.72 (3H, s), 6.37 (1H, d, J=3), 6.71 (1H, d, J=8), 6.98 (1H, d, J=3), 7.02 (1H, d, J=8).

DESCRIPTION 18

N-(1-Methyl-1H-indol-5-yl)-N'-(3-benzyloxypyrid-2-yl)urea (D18)

The title compound was prepared from 5-amino-1-methyl-1H-indole (D3), carbonyl diimidazole and 2-amino-3-benzyloxypyridine using a procedure similar to that described in Example 1.

NMR (D$_6$-DMSO) δ: 3.80 (3H, s) 5.44 (2H, s) 6.40 (1H, d, J=6), 7.35 (7H, m), 7.61 (2H, dd, J=13,3), 7.80 (2H, d, J=3), 7.94 (2H, d, J=6).

DESCRIPTION 19

3-Ethyl-2-methyl-5-nitro-1H-indole, (D19)

The title compound was prepared using a procedure identical to that described by P. Fludzinski et al. in J. Med. Chem., 1986, 29, 2415.

DESCRIPTION 20

1,3-Diethyl-2-methyl-5-nitro-1H-indole (D20)

The title compound was prepared in 92% yield from the nitroindole (D19), sodium hydride, and iodoethane using a procedure similar to that described in Description 2.

NMR (CDCl$_3$) δ: 1.23 (3H, t, J=8), 1.36 (3H, t, J=8), 2.40 (3H, s), 2.73 (2H, q, J=8), 4.12 (2H, q, J=8), 7.21 (1H, d, J=9), 8.02 (1H, dd, J=9, 2), 8.49 (1H, d, J=2).

DESCRIPTION 21

5-Amino-1,3-diethyl-2-methyl-1H-indole (D21)

The title compound was prepared in 86% yield from the nitroindole (D20) using a procedure similar to that in Description 3.

NMR (CDCl$_3$) δ: 1.22 (3H, t, J=8), 1.37 (3H, t, J=8), 2.39 (3H, s), 2.75 (2H, q, J=8), 4.14 (2H, q, J=8), 7.26 (1H, d, J=8), 8.04 (1H, dd, J=8, 1), 8.50 (1H, d, J=1).

DESCRIPTION 22

2-Methyl-5-nitro-3-propyl-1H-indole (D22)

The title compound was prepared in 94% yield from the 4-nitrophenylhydrazone of 2-hexanone using the method of Fludzinski et al described in J. Med. Chem., 1986, 29, 2415.

NMR (CDCl$_3$) δ: 0.94 (3H, t, J=8), 1.65 (2H, m, J=8), 2.38 (3H, s), 2.65 (2H, t, J=8), 7.22 (1H, d, J=9), 7.98 (1H, dd, J=9, 2), 8.15 (1H, s), 8.45 (1H, d, J=2).

DESCRIPTION 23

1,2-Dimethyl-5-nitro-3-propyl-1H-indole (D23)

The title compound was prepared in 89% yield from the nitroindole (D22) using a procedure similar to that in Description 2.

NMR (CDCl$_3$) δ: 0.90 (3H, t, J=8), 1.55 (2H, m, J=8), 2.34 (3H, s), 2.70 (2H, t, J=8), 3.72 (3H, s), 7.55 (1H, d, J=9), 7.92 (1H, dd, J=9, 2), 8.35 (1H, d, J=2).

DESCRIPTION 24

5-Amino-1,2-dimethyl-3-propyl-1H-indole (D24)

The title compound was prepared in 92% yield from the nitroindole (D23) using a procedure similar to that in Description 3.

NMR (CDCl$_3$) δ: 1.10 (3H, t, J=8), 1.75 (2H, m, J=8), 2.42 (3H, s), 2.75 (2H, t, J=8), 3.65 (3H, s), 3.95 (2H, s), 6.65 (1H, d, J=9), 6.92 (1H, s), 7.14 (1H, d, J=9).

DESCRIPTION 25

3-n-Hexyl-2-methyl-5-nitro-1H-indole (D25)

The title compound was prepared in 72% yield from the 4-nitrophenylhydrazone of 2-nonanone using the method of Fludzinski et al described in J. Med. Chem., 1986, 29, 2415.

NMR (CDCl$_3$) δ: 0.90 (3H, m), 1.30 (6H, m), 1.60 (2H, m), 2.42 (3H, s), 2.68 (2H, t, J=7), 7.22 (1H, m), 8.04 (1H, m), 8.20 (1H, s), 8.45 (1H, d, J=1).

DESCRIPTION 26

1,2-Dimethyl-3-n-hexyl-5-nitro-1H-indole (D26)

The title compound was prepared in 74% yield from the nitroindole (D25) using a procedure similar to that in Description 2.

NMR (CDCl$_3$) δ: 0.88 (3H, m), 1.30 (6H, m), 1.58 (2H, m), 2.35 (3H, s), 2.70 (2H, m), 3.65 (3H, s), 7.15 (1H, d, J=9), 7.94 (1H, m), 8.46 (1H, d, J=1).

DESCRIPTION 27

5-Amino-1,2-dimethyl-3-n-hexyl-1H-indole (D27)

The title compound was prepared in 84% yield from the nitroindole (D26) using a procedure similar to that in Description 3.

NMR (CDCl$_3$) δ: 0.88 (3H, m), 1.30 (6H, m), 1.55 (2H, m), 2.28 (3H, s), 2.62 (2H, t, J=8), 2.98 (2H, s), 3.55 (3H, s), 6.58 (1H, m), 6.80 (1H, d, J=1), 7.0 (1H, d, J=8).

DESCRIPTION 28

Ethyl 2-Oxopentanoate (D28)

The sodium salt of 2-oxopentanoic acid (1.00 g, 7.25 mM) was taken up in water and acidified to pH 1. The solution was extracted with ethyl acetate (3×100 ml), dried and solvents removed in vacuo. The resulting oil (0.67 g) was taken up in ethanol (50 ml) and Amberlyst 15 added (0.67 g). The suspension was stirred over 48 h, the resin filtered off and solvents removed in vacuo to give the title compound as a slightly coloured oil (0.54 g; 64%).

NMR (CDCl$_3$) δ: 0.95 (3H, t, J=7), 1.38 (3H, t, J=7), 1.55 (2H, m), 2.32 (2H, t, J=6), 4.32 (2H, q, J=7).

DESCRIPTION 29

Ethyl 2-oxopentanoate 4-nitrophenylhydrazone (D29)

To a solution of the ester (D28) (0.53 g, 3.6 mM) in ethanol (20 ml) was added 4-nitrophenylhydrazine (0.56 g, 3.6 mM) and the suspension stirred for 0.5 h. Concentrated hydrochloric acid (2 ml) was added to give a brown solution. After stirring for 0.5 h the solution was cooled in ice and the precipitated title compound filtered off (0.72 g; 69%).

NMR (CDCl$_3$) δ: 1.02 (3H, m), 1.40 (3H, m), 1.62 (2H, m), 2.60 (2H, m), 4.32 (2H, m), 7.28 (2H, m), 8.15 (2H, m), 8.30 (1H, s).

DESCRIPTION 30

3-Ethyl-5-nitro-1H-indole (D30)

The 4-nitrophenylhydrazone of ethyl 2-oxopentanoate (D29) (0.72 g, 2.60 mM) was heated to reflux for 16 h in concentrated hydrochloric acid. After cooling to room temperature the precipitated solid was filtered off. Chromatography on silica using dichloromethane as eluant gave the title compound as a yellow solid (0.22 g; 45%).

NMR (CDCl$_3$) δ: 1.35 (3H, t, J=8), 2.80 (2H, q, J=7), 7.12 (1H, m), 7.40 (1H, d, J=10), 8.12 (1H, dd, J=6, 1), 8.44 (1H, s), 8.60 (1H, m).

DESCRIPTION 31

3-Ethyl-1-methyl-5-nitro-1H-indole (D31)

The title compound was prepared in 95% yield from the corresponding indole (D30) following a procedure similar to that in Description 2.

NMR (CDCl$_3$) δ: 1.3 (3H t, J=7) 2.0 (2H, q, J=7), 3.82 (3H, s), 6.98 (1H, s), 7.27 (1H, d, J=8), 8.12 (1H, dd, J=7, 1), 8.55 (1H, d, J=1).
Found: M+ 204.
C$_{16}$H$_{12}$N$_2$O$_2$ requires 204.

DESCRIPTION 32

5-Amino-3-ethyl-1-methyl-1H-indole (D32)

The title compound was prepared from the corresponding nitro-indole (D31) in 98% yield following a procedure similar to that in Description 3.
NMR (CDCl$_3$) δ: 1.25 (3H, m), 2.70 (2H, q, J=8), 3.64 (3H, s), 6.62 (1H, m), 6.71 (1H, s), 6.78 (1H, m), 7.06 (1H, m).

DESCRIPTION 33

Phenyl N-(1-Methyl-1H-indol-5-yl)carbamate (D33)

To a solution of phenyl chloroformate (2.21 ml; 17.4 mM) in dry tetrahydrofuran (30 ml), cooled in a carbon tetrachloride/solid carbon dioxide bath, was added 5-amino-1-methylindole (D3) (2.31 g; 15.8 mM) followed by triethylamine (2.40 ml; 17.4 mM). The mixture was stirred for 45 min at −20° C. (bath temp.), then evaporated and the residue was dissolved in ethyl acetate, washed with brine, dried and evaporated to give the title compound (4.29 g; 100%), m.p. 103°–107° C. (EtOAc/petrol).
NMR (CDCl$_3$) δ: 3.80 (3H, s), 6.45 (1H, d, J=3), 6.93 (1H, broad s), 7.05 (1H, d, J=3), 7.25 (5H, m), 7.40 (2H, dd, J=8, 8), 7.74 (1H, broad s).

DESCRIPTION 34

2-Dimethylamino-5-nitropyridine (D34)

2-Chloro-5-nitropyridine (1.58 g, 10 mM) was treated with a 33% w/w solution of dimethylamine in methylated spirit (18 ml, 100 mM). An exothermic reaction ensued, with formation of a yellow solid. After 0.5 h the solid was filtered off. The filtrate was evaporated and the residue was combined with the yellow solid, and all material was dissolved in dichloromethane. This solution was washed with water and brine, dried and evaporated, to give the title compound (1.64 g; 98%), m.p. 146°–149° C.
NMR (CDCl$_3$) δ: 3.25 (6H, s), 6.48 (1H, d, J=10), 8.20 (1H, dd, J=10,3), 9.06 (1H, d, J=3).
Found: M+ 167.
C$_7$H$_9$N$_3$O$_2$ requires 167.

DESCRIPTION 35

5-Amino-2-dimethylaminopyridine (D35)

2-Dimethylamino-5-nitropyridine (D34) (1.64 g, 9.8 mM) was stirred with 10% palladium on charcoal (0.16 g) in ethanol (200 ml) under 1 atmos. of hydrogen. After 6 h the catalyst was filtered off onto Kieselguhr and the filtrate was evaporated. The residue was dissolved in diethyl ether, filtered again, and chromatographed on silica gel (50 g) using ether as eluant. The eluted product was purified further by extraction with petrol (bp 60°–80° C.) to give the title compound as a reddish oil (0.66 g; 49%).
NMR (CDCl$_3$) δ: 3.00 (6H, s), 6.47 (1H, d, J=9), 6.99 (1H, dd, J=9,3), 7.78 (1H, d, J=3).
Found: M+ 137.
C$_7$H$_{11}$N$_3$ requires 137.

DESCRIPTION 36

3-Isopropyl-2-methyl-5-nitro-1H-indole (D36)

The title compound was prepared in 62% yield from the 4-nitrophenyl hydrazone of 4-methyl-2-pentanone using the method of Fludzinski et al described in J. Med. Chem., 1986, 29, 2415.
NMR (CDCl$_3$) δ: 1.42 (6H, d, J=6), 2.42 (3H, s), 3.20 (1H, m), 7.28 (1H, m), 8.03 (1H, dd, J=7, 1), 8.12 (1H, s), 8.60 (1H, m).

DESCRIPTION 37

1,2-Dimethyl-3-isopropyl-5-nitro-1H-indole (D37)

The title compound was formed in 85% yield from the nitroindole (D36) following a procedure similar to that in Description 2.
NMR (CDCl$_3$) δ: 1.47 (6H, d, J=7), 2.42 (3H, s), 3.20 (1H, m), 3.68 (3H, s), 7.24 (1H, m), 8.04 (1H, m), 8.62 (1H, m).

DESCRIPTION 38

5-Amino-1,2-dimethyl-3-isopropyl-1H-indole (D38)

The title compound was formed in 57% yield from the nitroindole (D37) following a procedure similar to that in Description 3.
NMR (CDCl$_3$) δ: 1.35 (6H, d, J=7), 2.30 (3H, s), 3.15 (1H, m), 3.55 (3H, s), 6.60 (1H, m), 7.05 (2H, m).

EXAMPLE 1

N-(1,2-Dimethyl-3-ethyl-1H-indol-5-yl)-N'-(3-pyridyl)urea hydrochloride (E1)

To a solution of the aminoindole (D1) (0.71 g; 3.78 mM) in dichloromethane (13.5 ml) at 0° C. was added a 12.5% solution of phosgene in toluene (3.28 ml; 3.79 mM). After stirring for 0.5 h, triethylamine (1.15 ml) was added and stirring was continued for 0.5 h. A solution of 3-aminopyridine (0.34 g; 3.6 mM) in dichloromethane (10 ml) was then added, and stirring continued for 3.5 h at room temperature. Several drops of aqueous sodium hydroxide were added to the reaction mixture which was vigorously stirred for 0.5 h. The reaction mixture was diluted with water and extracted with dichloromethane. The combined organic extracts were washed with brine, dried over sodium sulphate and evaporated to dryness. Chromatography on silica using dichloromethane as eluant afforded the title compound (0.2 g; 17%) which was converted to the hydrochloride salt using hydrogen chloride in ether/ethanol, m.p. 158°–165° C.
NMR (D$_6$-DMSO) δ: 1.12 (3H, t, J=8), 2.31 (3H, s), 2.63 (2H, q, J=8), 3.61 (3H, s), 7.02 (1H, m), 7.28 (1H, d, J=10), 7.64 (1H, s), 7.89 (1H, m), 8.31 (1H, m), 8.45 (1H, d, J=6), 9.13 (1H, s), 9.22 (1H, s), 10.12 (1H, s).
Found: M+ 308.1640.
C$_{18}$H$_{20}$N$_4$O requires 308.1637.

EXAMPLE 2

N-(1-Methyl-1H-indol-5-yl)-N'- (3-pyridyl)urea hydrochloride (E2)

Method A

The title compound was prepared from 5-amino-1-methyl-1H-indole(D3), phosgene and 3-aminopyridine using a procedure similar to that described for Example 1, in 27% yield m.p. 175°–180° C.
NMR (d$_6$-DMSO) δ: 3.76 (3H, s), 6.34 (1H, d, J=2), 7.16 (1H, dd, J=8, 2), 7.29 (1H, d, J=2), 7.37 (1H, d, J=8), 7.70 (1H, s), 7.87 (1H, dd, J=8, 8), 8.30 (1H, m), 8.45 (1H, J=8), 9.08 (1H, m), 9.24 (1H, s), 10.03 (1H, s).

Found: M+ 266. 1667.

C₁₅H₁₄N₄O requires 266.1667.

Method B

A solution of the aminoindole (D3)(1.95 g; 13 mM) in dichloromethane (20 ml) was added dropwise to a solution of 3-pyridyl isocyanate (D4) (prepared from 3-pyridinecarbonyl azide (2.14 g; 15 mM) in toluene) at room temperature. The reaction mixture was stirred for 17 h, then cooled, and the precipitate filtered off to give the crude product (3.36 g; 95%). This was dissolved in hot ethanol and ethereal hydrogen chloride added to afford the title compound as its hydrochloride salt (3.1 g; 80%) identical with the material prepared by method A.

EXAMPLE 3

N-(1,2,3-Trimethyl-1H-indol-5-yl)-N'-(3-pyridyl)urea hydrochloride (E3)

The title compound was prepared in 51% yield from 5-amino-1,2,3-trimethyl-1H-indole (D6), phosgene and 3-aminopyridine using a procedure similar to that in Example 1, m.p. 330° C.

NMR (D₆-DMSO) δ: 2.12 (3H, s), 2.30 (3H, s), 3.60 (3H, s), 7.04 (1H, dd, J=9, 2), 7.27 (1H, d, J=9), 7.58 (1H, d, J=2), 7.89 (1H, dd, J=9, 9), 8.32 (1H, m), 8.44 (1H, d, J=6), 9.11 (1H, d, J=2), 9.28 (1H, s), 10.22 (1H, s).

Found: M+ 294.1485.

C₁₇H₁₈N₄O requires: 294.1481.

EXAMPLE 4

N-(1-Propyl-1H-indol-5-yl)-N'-(3-pyridyl)urea oxalate (E4)

The title compound was prepared in 43% yield from 5-amino-1-propyl-1H-indole (D8) and 3-pyridyl isocyanate (D4) using a procedure similar to that in Example 2 (Method B), the product being isolated as the oxalate salt, m.p. 165°-169° C.

NMR (D₆ DMSO) δ: 0.82 (3H, t, J=7), 1.76 (2H, h, J=7), 4.10 (2H, t, J=7), 6.37 (1H, d, J=3), 7.13 (1H, d, J=9), 7.34 (1H, d, J=3), 7.40 (1H, d, J=9), 7.44 (1H, m), 7.69 (1H, s), 8.05 (1H, m), 8.24 (1H, d, J=6), 8.67 (1H, s), 8.73 (1H, d, J=2), 8.97 (1H, s).

Found: M+ 294.1485.

C₁₇H₁₈N₄O requires: 294.1481.

EXAMPLE 5

N-(1-Methyl-1H-indol-4-yl)-N'-(3-pyridyl)urea hydrochloride (E5)

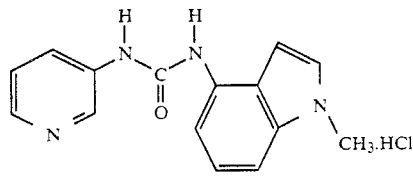

A solution of the aminoindole (D10) (0.44 g; 3.01 mM) in dichloromethane (10 ml) was added dropwise to a solution of 3-pyridyl isocyanate (D4) (prepared from 3-pyridine carbonyl azide (0.51 g; 3.4 mM) in toluene) at room temperature. The reaction mixture was stirred for 17 h, then cooled and the precipitate filtered off to give the crude product (1 g; 100%). This was dissolved in hot ethanol and ethereal hydrogen chloride added to afford the title compound as its hydrochloride salt (0.74 g; 81%), m.p 238° C.

NMR (D₆ DMSO) δ: 3.79 (3H, s), 6.80 (1H, d, J=3), 7.11 (2H, dd, J=6, 6), 7.30 (1H, d, J=3), 7.70 (1H, dd, J=6, 2), 7.90 (1H, m), 8.33 (1H, d, J=6), 8.49 (1H, d, J=3), 9.13 (1H, d, J=2), 9.40 (1H, s), 10.80 (1H, s).

Found: M+ 266.1170.

C₁₅H₁₄N₄O requires: 266.1167.

EXAMPLE 6

N-(1-Methyl-1H-indol-6-yl)-N'-(3-pyridyl)urea hydrochloride (E6)

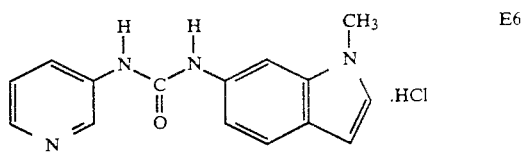

A solution of the aminoindole (D12) (0.3 g; 2.05 mM) in dichloromethane (10 ml) was added dropwise to a solution of 3-pyridyl isocyanate (D4) (prepared from 3-pyridinecarbonyl azide (0.28 g; 2.26 mM) in toluene) at room temperature. The reaction mixture was stirred for 17 h, then cooled, and the precipitate filtered off to give the crude product (0.43 g; 79%). This was dissolved in hot ethanol and ethereal hydrogen chloride added to afford the title compound as the hydrochloride salt (0.35 g; 56%), m.p. 215° C.

NMR (CDCl₃) δ: 3.73 (3H, s), 6.36 (1H, d, J=2), 6.96 (1H, dd, J=11, 2), 7.24 (1H, d, J=2), 7.45 (1H, d, J=11), 7.75 (1H, d, J=3), 7.90 (1H, m), 8.32 (1H, d, J=8), 8.46 (1H, d, J=3), 9.13 (1H, d, J=3), 9.49 (1H, s), 10.25 (1H, s).

| Found: | C, 59.24; | H, 4.96; | N, 18.38. |
|---|---|---|---|
| C₁₅H₁₅N₄OCl requires: | C, 59.50; | H, 4.99; | N, 18.51. |

EXAMPLE 7

N-(1H-Indol-5-yl)-N'-(3-pyridyl)urea hydrochloride (E7)

Method A

A solution of commercially available 5-aminoindole (0.5 g; 3.8 mM) in dichloromethane (5 ml) was added dropwise to a solution of 3-pyridyl isocyanate (D4) (prepared from 3-pyridinecarbonyl azide (0.62 g; 4.2 mM) in toluene) at room temperature. The reaction mixture was stirred for 2 days, then cooled and the precipitate filtered off, to give the crude product (0.54 g; 57%), which was dissolved in ethanol and converted to the hydrochloride salt using hydrogen chloride in ether, m.p. 180°-185° C.

NMR (D₆-DMSO) δ: 6.38 (1H, s), 7.11 (1H, d, J=8), 7.35 (2H, m), 7.7 (1H, s), 7.92 (1H, m), 8.35 (1H, d, J=8), 8.49 (1H, d, J=3), 9.12 (1H, s), 9.39 (1H, s), 10.41 (1H, s), 11.7 (1H, s).

Found: M+ 252.

C₁₄H₁₂N₄O requires 252.

Method B

Compound E7 may also be prepared by reacting 3-methyl-4-nitroaniline with 3-pyridyl isocyanate (D4)

by the procedure of Method A. The resulting nitrophenyl urea may be subjected to a Leimgruber synthesis by condensation with dimethylformamide dimethylacetal with heating followed by hydrogenation over palladium and charcoal at high pressure to effect formation of the indole.

EXAMPLE 8

N-(1-Methyl-1H-indol-5-yl)-N'-methyl-N'-(3-pyridyl)urea (E8)

To a solution of carbonyl diimidazole (1.22 g; 7.5 mM) in dichloromethane (10 ml) was added aminoindole (D3) (1.0 g; 6.85 mM) in dichloromethane (10 ml). After stirring at room temperature for 15 min, the solution was evaporated to dryness. The residue was taken up in dimethylformamide (10 ml) and to this solution was added 3-methylaminopyridine (D13) (0.74 g; 6.2 mM) in dimethylformamide (10 ml). The reaction mixture was heated to 90° C. for 1 h, then cooled and added dropwise to water (200 ml) with vigorous stirring. After cooling overnight, the precipitate was filtered and dried to give the crude product (1.99 g). Chromatography on silica using dichloromethane as eluant afforded the title compound (0.81 g; 42%), m.p. 58°-60° C.

NMR (CDCl₃) δ: 3.40 (3H, s), 3.75 (3H, s), 6.18 (1H, s), 6.39 (1H, d, J=3), 7.02 (1H, d, J=3), 7.09 (1H, dd, J=8, 1), 7.21 (1H, d, J=8), 7.42 (1H, m), 7.57 (1H, d, J=1), 7.75 (1H, m), 8.59 (1H, dd, J=3,1), 8.70 (1H, d, J=1).

Found: M⁺ 280.

C₁₆H₁₆N₄O requires 280.

EXAMPLE 9

N-Methyl-N-(1-methyl-1H-indol-5-yl)-N'-(3-pyridyl)urea (E9)

The title compound was prepared from 1-methyl-5-methylamino-1H-indole (D15) and 3-pyridyl isocyanate (D4) using a procedure similar to that described for Example 2 Method B. The crude produce was obtained in 45% yield.

Recrystallisation from ethanol afforded the title compound, m.p. 168°-170° C.

NMR (CDCl₃) δ: 3.39 (3H, s), 3.87 (3H, s), 6.35 (1H, s), 6.55 (1H, d, J=3), 7.18 (3H, m), 7.43 (1H, d, J=8), 7.60 (1H, d, J=1), 8.01 (1H, m), 8.2 (2H, m).

Found: C, 68.55; H, 5.79; N, 19.92%.

C₁₆H₁₆N₄O requires C, 68.55; H, 5.75; N, 19.99%.

EXAMPLE 10

N-Methyl-N-(1-methyl-1H-indol-5-yl)-N'-methyl-N'-(3-pyridyl)urea (E10)

To a suspension of 80% sodium hydride (0.06 g; 2 mM) in dimethylformamide (5 ml), was added the monomethyl urea (E9) (0.5 g; 1.79 mM). After stirring at room temperature for 0.5 h, methyl iodide (0.12 ml; 1.93 mM) was added dropwise. Stirring was continued at room temperature for 1 h, then heated at 50° C. for 1 h. The reaction mixture was cooled in ice, then quenched with water. The mixture was then extracted with dichloromethane, washed with water, dried over sodium sulphate and evaporated to give the crude product (0.59 g). Chromatography on silica using dichloromethane as eluant afforded the title compound (0.31 g; 60%) which was recrystallised from cyclohexane to give a white solid (160 mg) m.p. 91°-92.5° C.

NMR (CDCl₃) δ: 3.18 (3H, s), 3.25 (3H, s), 3.71 (3H, s), 6.3 (1H, d, J=3), 6.6 (1H, dd, J=8,1), 6.85 (1H, m), 7.01 (4H, m), 8.10 (2H, m).

Found: C, 69.57; H, 6.21; N, 19.04%.

C₁₇H₁₈N₄O requires C, 69.37; H, 6.16; N, 19.03%.

EXAMPLE 11

N-(1-Methyl-1H-indol-5-yl)-N'-(2-pyridyl)urea (E11)

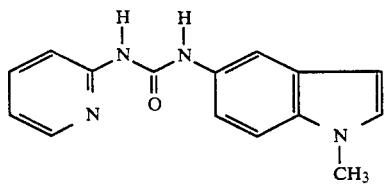

E11

The title compound was prepared from 5-amino-1-methylindole (D3) and 2-aminopyridine using a procedure similar to that described for Example 8. The crude product was obtained in 83% yield. Recrystallisation from ethanol afforded the title compound in 70% yield, m.p. 182°-185° C.

NMR (CDCl₃) δ: 3.8 (3H, s), 6.42 (1H, d, J=3), 6.9 (1H, m), 7.05 (1H, d, J=1), 7.2 (1H, d, J=8), 7.25 (1H, d, J=1), 7.32 (1H, dd, J=8, 1), 7.61 (1H, m), 7.88 (1H, s), 8.25 (1H, d, J=3), 9.11 (1H, s), 11.18 (1H, s).

Found: M⁺ 266.

C₁₅H₁₄N₄O requires 266.

EXAMPLE 12

N-(1,4-Dimethyl-1H-indol-5-yl)-N'-(3-pyridyl)urea hydrochloride (E12)

The title compound was prepared from 5-amino-1,4-dimethylindole (D17) and 3-pyridyl isocyanate (D4) following the procedure described in Example 2 Method B. This gave a yellow-green powder in 21% yield.

NMR (D₆-DMSO) δ: 2.38 (3H, s), 3.76 (3H, s), 6.45 (1H, d, J=3), 7.24 (2H, s), 7.30 (1H, d, J=3), 7.89 (1H, dd, J=8,5), 8.33 (1H, d, J=8), 8.44 (1H, d, J=5), 8.67 (1H, s), 9.11 (1H, fine d), 10.3 (1H, b s).

Found: M⁺ 280.

C₁₆H₁₆N₄O requires 280.

Found: C, 57.8; H, 5.5; N, 16.9%. C₁₆H₁₆N₄O .HCl.H₂O requires C, 54.4, H, 5.7; N, 16.7%.

EXAMPLE 13

N-(1-Methyl-1H-indol-5-yl)-N'-(2-chloropyrid-3-yl)urea hydrochloride (E13)

A stirred suspension of carbonyl diimidazole (0.34 g, 2.1 mM) in dry dichloromethane (5 ml) was treated with a solution of 5-amino-1-methyl-1H-indole (D3) (0.29 g, 2 mM) in dry dichloromethane (5 ml). After 0.25 h the reaction mixture was evaporated to dryness, and the residue dissolved in dimethylformamide (10 ml). 3-Amino-2-chloro-pyridine (0.23 g, 22 mM) was added to the reaction mixture which was heated to 90° C. for 1 h, then cooled and added to water (200 ml) with vigorous stirring. The precipitate was filtered, dried and recrystallised from ethanol affording the title compound as an off white solid (0.25 g; 42%) which was converted to the hydrochloride salt using hydrogen chloride in ether, m.p. 155° C.

NMR (D₆-DMSO) δ: 3.78 (3H, s), 6.37 (1H, d, J=5), 7.15 (1H, dd, J=12, 3), 7.30 (1H, d, J=5), 7.40 (2H, m), 7.72 (1H, d, J=3), 8.02 (1H, d, J=5), 8.49 (1H, d, J=3), 8.6 (1H, d, J=12), 9.34 (1H, s).
Found: M+ 299, 301.
$C_{15}H_{13}N_4O$ Cl requires 299, 301.

EXAMPLE 14

N-(1-Methyl-1H-indol-5-yl)-N'-(2-chloropyrid-5-yl)urea hydrochloride (E14)

The title compound was prepared in 60% yield from 5-amino-1-methyl-1H-indole (D3), carbonyl diimidazole and 5-amino-2-chloropyridine, using a procedure similar to that described in Example 13. m.p. 212° C.

NMR ($D_6$-DMSO) δ: 3.78 (3H, s), 6.32 (1H, d, J=5), 7.15 (1H, dd, J=12,3), 7.28 (1H, d, J=5), 7.40 (2H, m), 7.70 (1H, d, J=3), 8.00 (1H, dd, J=12,5), 8.50 (1H, d, J=5).
Found: M+ 299, 301.
$C_{15}H_{13}N_4O$ Cl requires 299, 301.

EXAMPLE 15

N-(1-Methyl-1H-indol-5-yl)-N'-(3-hydroxypyrid-2-yl)urea hydrochloride (E15)

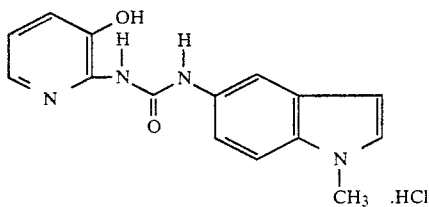

E15

N-(1-Methyl-1H-indol-5-yl)-N'-(3-benzyloxypyrid-2-yl)urea (D18) (0.37 g, 1 mM) was hydrogenated for 2 h in ethanol (40 ml) at atmospheric pressure and room temperature. The reaction mixture was filtered through kieselguhr, washed with ethanol. The filtrate was evaporated in vacuo to afford the title compound (0.21 g, 74%) which was converted to the hydrochloride salt using hydrogen chloride in ether. m.p. 223° C.

NMR ($D_6$-DMSO) δ: 3.78 (3H, s), 6.39 (1H, d, J=5), 6.95 (1H, m), 7.23 (2H, m), 7.3 (1H, d, J=5), 7.39 (1H, d, J=12), 7.83 (2H, m), 7.95 (1H, s).
Found: M+ 282.
$C_{15}H_{14}N_4O_2$ requires 282.

EXAMPLE 16

N-(1,3-Diethyl-2-methyl-1H-indol-5-yl)-N'-(3-pyridyl)urea (E16)

The title compound was prepared from the aminoindole (D21) and 3-pyridyl isocyanate (D4) using a procedure similar to that described for Example 2 Method B. The crude product was obtained in 79% yield. Recrystallisation from ethanol afforded the title compound, m.p. 192°-193° C. NMR ($D_6$ DMSO) δ: 1.12 (3H, t, J=8), 1.20 (3H, t, J=8), 2.31 (3H, s), 2.65 (2H, q, J=8), 4.09 (2H, q, J=8), 7.02 (1H, dd, J=9,3), 7.26 (1H, d, J=9), 7.29 (1H, m), 7.63 (1H, d, J=3), 7.98 (1H, m), 8.17 (1H, m), 8.55 (1H, s), 8.60 (1H, d, J=3), 8.74 (1H, s).

EXAMPLE 17

N-(1,2-Dimethyl-3-propyl-1H-indol-5-yl)-N'-(3-pyridyl)urea hydrochloride (E17)

The title compound was prepared from the aminoindole (D24) and 3-pyridyl isocyanate (D4) using a procedure similar to that described for Example 2 Method B, m.p. 132°-134° C.

NMR ($D_6$-DMSO) δ: 0.88 (3H, t, J=8), 1.54 (2H, m), 2.28 (3H, s), 2.58 (2H, m), 3.62 (3H, s), 7.04 (1H, d, J=4), 7.28 (1H, d, J=6), 7.60 (1H, s), 7.90 (1H, m), 8.32 (1H, d, J=4 ), 8.45 (1H, d, J=6), 9.12 (1H, s), 9.25 (1H, s), 10.22 (1H, s).
Found: M+ 322.
$C_{19}H_{22}N_4O$ requires 322.

EXAMPLE 18

N-(1,2-Dimethyl-3-n-hexyl-1H-indol-5-yl)-N'-(3-pyridyl)urea (E18)

The title compound was prepared from the aminoindole (D27) and 3-pyridyl isocyanate (D4) using a procedure similar to that described for Example 2 Method B, the product being isolated as the free base.

NMR ($D_6$ DMSO) δ: 0.84 (3H, m), 1.25 (6H, m), 1.52 (2H, m), 2.30 (3H, s), 2.62 (2H, m), 3.58 (3H, s), 7.05 (1H, dd, J=8, 2), 7.28 (1H, d, J=6), 7.60 (1H, s), 7.90 (1H, m), 8.32 (1H, m), 8.45 (1H, d, J=6), 9.15 (1H, m), 9.25 (1H, s), 10.15 (1H, s).

EXAMPLE 19

N-(1-Methyl-1H-indol-4-yl)-N'-(4-pyridyl)urea hydrochloride (E19)

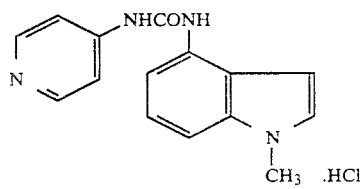

E19

4-Amino-1-methyl-1H-indole (D10) (0.44 g) was treated successively with phosgene (solution in toluene) and 4-aminopyridine as described in Example 1. The reaction mixture was partitioned between dichloromethane and water, and filtered. The solid, the crude free base of the title compound, was filtered off and dried in vacuo. The filtrate was separated, and the organic portion was washed with brine, dried and evaporated to give an oil. The oil was chromatographed on silica using methanol/chloroform (0–10% methanol, gradient) as eluant, giving further crude free base.

The two portions of free base were combined, and this material (0.49 g) was suspended in ethanol (50 ml) at reflux. Briefly after removing from the steam bath, HCl in ether (1.1 M, 3 ml) was added. The suspension was brought back to reflux, and then cooled. Filtration and drying gave the title compound (0.30 g) as a greybrown solid. NMR ($D_6$-DMSO) δ: 3.80 (3H, s), 6.87 (1H, d, J=3), 7.15 (2H, m), 7.32 (1H, d, J=3), 7.73 (1H, d, J=7), 7.95 (2H, d, J=6), 8.60 (2H, d, J=6), 9.76 (1H, s), 11.84 (1H, s), 14.5 (v broad).
Found: M+ 266, $C_{15}H_{14}N_4O$ requires 266.
Found: C, 55.89; H, 5.15; N, 17.20%.
$C_{15}H_{14}N_4O.HCl.H_2O$ requires C, 56,16; H, 5.34; N, 17.47%.

EXAMPLE 20

N-(3-Ethyl-1-methyl-1H-indol-5-yl)-N'-(3-pyridyl)urea (E20)

The title compound was prepared in 82% yield from the aminoindole (D32) and 3-pyridyl isocyanate (D4)

using a procedure similar to that described for Example 2, Method B, the product being isolated as the free base.

NMR (CDCl₃) δ: 1.26 (3H, t, J=7), 2.68 (2H, q, J=7), 3.69 (3H, s), 6.85 (1H, s), 7.04 (1H, m), 7.30 (2H, m), 7.56 (1H, s), 7.95 (1H, m), 8.15 (1H, m), 8.65 (2H, m), 8.80 (1H, s).

Found: M+ 294, C₁₇H₁₈N₄O requires 294.

EXAMPLE 21

N-(1,2-Dimethyl-3-ethyl-1H-indol-5-yl)-N'-(2-pyridyl)urea (E21)

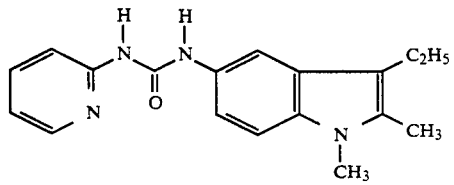

The title compound was prepared from the aminoindole (D1), phosgene and 2-aminopyridine using a procedure similar to that described for Example 1, the product being isolated as the free base, m.p. 120°-123° C.

NMR (CDCl₃) δ: 1.22 (3H, t, J=8), 2.35 (3H, s), 2.73 (2H, q, J=8), 3.64 (3H, s), 6.91 (2H, m), 7.19 (1H, d, J=9), 7.28 (1H, m), 7.60 (1H, m), 7.77 (1H, m), 8.27 (2H, m), 11.5 (1H, broad s).

Found: C, 70.03; H, 6.36; N, 17.97%.
C₁₈H₂₀N₄O requires C, 70.11; H, 6.54; N, 18.17%.

EXAMPLE 22

N-(1,2-Dimethyl-3-ethyl-1H-indol-5-yl)-N'-(4-pyridyl)urea hydrochloride (E22)

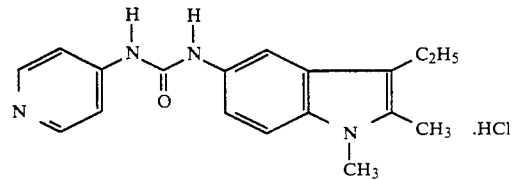

The title compound was prepared in 47% yield from the aminoindole (D1), phosgene and 4-aminopyridine using a procedure similar to that described for Example 1, the product being isolated as the hydrochloride salt, m.p. 237°-243° C.

NMR (D₆ DMSO) δ: 1.12 (3H, t, J=8), 2.30 (3H, s), 2.62 (2H, q, J=8), 3.61 (3H, s), 7.05 (1H, dd, J=9,2), 7.29 (1H, d, J=9), 7.64 (1H, d, J=2), 7.90 (2H, d, J=6), 8.57 (2H, d, J=6), 9.67 (1H, broad s), 11.28 (1H, broad s).

Found: M+ 308.
C₁₈H₂₀N₄O requires 308.

EXAMPLE 23

N-(1-Methyl-1H-indol-5-yl)-N'-(2-dimethylamino-5-pyridyl)urea (E23)

5-Amino-2-dimethylaminopyridine (D35) (0.137 g; 1 mM) was stirred with 80% sodium hydride (66 mg; 2.2 mM) in dry dimethylformamide (5 ml) for 15 min at room temperature under nitrogen. The phenyl carbamate (D33) was then added and the mixture stirred overnight at room temperature. Solvent was then removed in vacuo and the residue was dissolved in dichloromethane/methanol, washed with water and brine, dried and evaporated. The residue was triturated with dichloromethane/petrol, and the solid material was chromatographed on silica gel and eluted with 2% methanol/dichloromethane. This gave the title compound (60 mg; 19%), m.p. 220°-226° C.

NMR (D₆ DMSO) δ: 2.98 (6H, s), 3.75 (3H, s), 6.32 (1H, d, J=3), 6.62 (1H, d, J=9), 7.11 (1H, d, J=8), 7.26 (1H, d, J=3), 7.31 (1H, d, J=8), 7.66 (2H, m), 8.10 (1H, d, J=3), 8.20 (1H, s), 8.38 (1H, s).

Found: M+ 309.
C₁₇H₁₉N₅O requires 309.

EXAMPLE 24

N-1,2-Dimethyl-3-isopropyl-1H-indol-5-yl)-N'-pyridyl)urea hydrochloride (E24)

The title compound was prepared from the aminoindole (D38) and 3-pyridyl isocyanate (D4) using a procedure similar to that described for Example 2, Method B.

NMR (D₆ DMSO) δ: 1.42 (6H, d, J=7), 2.42 (3H, s), 3.22 (1H, m), 3.68 (3H, s), 7.12 (1H, m), 7.36 (1H, m), 7.90 (1H, s), 7.98 (1H, m), 8.38 (1H, m), 8.55 (1H, m), 9.20 (1H, s), 9.30 (1H, s), 10.22 (1H, s).

Found M+ 322.
C₁₉H₂₂N₄O requires 322.

EXAMPLE 25

N-(1,3-Diethyl-1H-indol-5-yl)-N'-(3-pyridyl)urea (E25)

The title compound was prepared from ethyl 1,3-diethyl-5-nitro-1H-indole-2-carboxylate by hydrolysis and decarboxylation, then using a procedure similar to that in Description 3 and Example 2, Method B, the product being isolated as the free base.

m.p. 164°-165° C.

NMR (CDCl₃) δ: 1.28 (3H, t, J=7), 1.45 (3H, t, J=7), 2.74 (2H, q, J=7), 4.12 (2H, q, J=7), 6.82 (1H, bs), 6.95 (1H, s), 7.10 (2H, m), 7.25 (2H, m), 7.58 (1H, s), 8.07 (1H, m), 8.24 (1H, m), 8.32 (1H, m).

Found: M+ 308.
C₁₈H₂₀N₄O requires 308.
Found: C, 69.93; H, 6.38; N, 17.98%.
C₁₈H₂₀N₄O requires C, 70.11; H, 6.54; N, 18.17%.

EXAMPLE 26

N-(3-Isopropyl-1-methyl-1H-indol-5-yl)-N'-(3-pyridyl)urea (E26)

The title compound was prepared from ethyl 3-isopropyl-1-methyl-5-nitro-1H-indole-2-carboxylate by hydrolysis and decarboxylation, then using a procedure similar to that in Description 3 and Example 2, Method B, the product being isolated as the free base.

NMR (CDCl₃) δ: 1.32 (6H, d, J=6), 3.15 (1H, m), 3.76 (3H, s), 6.76 (1H, bs), 6.88 (1H, s), 7.02 (1H, m), 7.13 (1H, m), 7.25 (2H, m), 7.60 (1H, m), 8.08 (1H, d, J=8), 8.22 (1H, m), 8.30 (1H, m).

Found: M+ 308.
C₁₈H₂₀N₄O requires 308.

EXAMPLE 27

N-(1,3-Dimethyl-1H-indol-5-yl)-N'-(3-pyridyl)urea (E27)

The title compound was prepared from ethyl 1,3-dimethyl-5-nitro-1H-indole-2-carboxylate by hydrolysis and decarboxylation, then using a procedure similar to that in Description 3 and Example 2, Method B, the product being isolated as the free base.

m.p. 210° C.

NMR (D6-DMSO) δ: 2.25 (3H, s), 3.72 (3H, s), 6.88 (1H, s), 7.10 (1H, dd, J=9, 1), 7.22 (2H, m), 7.69 (1H, d, J=1), 8.04 (1H, m), 8.16 (1H, m), 8.31 (1H, s), 8.68 (1H, m).

Found: M+ 280.

$C_{16}H_{16}N_4O$ requires 280.

TABLE 1

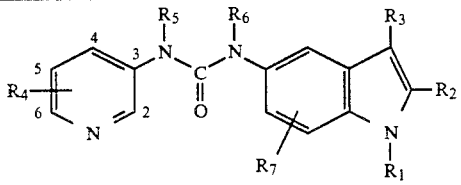

| | $R_1$ | $R_2$ | $R_3$ | $R_4$ | $R_5$ | $R_6$ | $R_7$ | Salt |
|---|---|---|---|---|---|---|---|---|
| E1 | $CH_3$ | $CH_3$ | $C_2H_5$ | H | H | H | H | HCl |
| E2 | $CH_3$ | H | H | H | H | H | H | HCl |
| E3 | $CH_3$ | $CH_3$ | $CH_3$ | H | H | H | H | HCl |
| E4 | $(CH_2)_2CH_3$ | H | H | H | H | H | H | $(COOH)_2$ |
| E7 | H | H | H | H | H | H | H | HCl |
| E8 | $CH_3$ | H | H | H | $CH_3$ | H | H | — |
| E9 | $CH_3$ | H | H | H | H | $CH_3$ | H | — |
| E10 | $CH_3$ | H | H | H | $CH_3$ | $CH_3$ | H | — |
| E12 | $CH_3$ | H | H | H | H | H | 4-$CH_3$ | HCl |
| E13 | $CH_3$ | H | H | 2-Cl | H | H | H | HCl |
| E14 | $CH_3$ | H | H | 6-Cl | H | H | H | HCl |
| E16 | $C_2H_5$ | $CH_3$ | $C_2H_5$ | H | H | H | H | — |
| E17 | $CH_3$ | $CH_3$ | $nC_3H_7$ | H | H | H | H | HCl |
| E18 | $CH_3$ | $CH_3$ | $nC_6H_{13}$ | H | H | H | H | — |
| E20 | $CH_3$ | H | $C_2H_5$ | H | H | H | H | — |
| E23 | $CH_3$ | H | H | 6-$N(CH_3)_2$ | H | H | H | — |
| E24 | $CH_3$ | $CH_3$ | $iC_3H_7$ | H | H | H | H | HCl |
| E25 | $C_2H_5$ | H | $C_2H_5$ | H | H | H | H | — |
| E26 | $CH_3$ | H | $iC_3H_7$ | H | H | H | H | — |
| E27 | $CH_3$ | H | $CH_3$ | H | H | H | H | — |

Pharmacological data

[³H]-mesulergine binding to pig choroid plexus membranes in vitro

Evidence from the literature suggests that 5-$HT_{1C}$ antagonists may have a number of therapeutic indications including the treatment of anxiety, migraine, depression, feeding disorders and obsessive compulsion disorders. (Curzon and Kennett, 1990; Fozard and Gray, 1989) and Alzheimer's Disease (Lawlor, 1989, J. Arch. Gen. Psychiat. Vol. 46 p.542).

The affinity of test drugs for the 5-$HT_{1C}$ binding site can be determined by assessing their ability to displace [³H]-mesulergine from 5-$HT_{1C}$ binding sites in pig choroid plexus membranes. The method employed was similar to that of Pazos et al, 1984.

Pooled pig choroid plexi were homogenised in 20 vols of Tris HCl buffer (pH7.4) (containing 4 mM $CaCl_2$ and 0.01% ascorbic acid) and centrifuged at 50,000 g for 15 rain at 4° C. The supernatant was removed and re-centrifuged. This was repeated a further two times with the incubation of the homogenate (37° C. for 15 min) before the final centrifugation. The final pellet was resuspended in 20 vols of buffer and stored at −70° C. until use.

The tissue suspension (50 µl) was incubated with [³H]-mesulergine (2 nM) in Tris HCl buffer (pH7.4) at 37° C. (containing 0.01% ascorbic acid, 4 mM $CaCl_2$) and $3 \times 10^{-8}$ M spiperone for 30 minutes. Non-specific binding was measured in the presence of mianserin ($10^{-6}$M). Six concentrations of test drug ($10^{-9}$ to $10^{-4}$ M final concentration) were added in a volume of 50 µl. The total assay volume was 500 µl. Incubation was stopped by rapid filtration using a Skatron cell harvester and radioactivity measured by liquid scintillation spectrometry. The $IC_{50}$ values were determined and the $pK_i$ (the negative logarithm of the inhibition constant) calculated from the Cheng Prusoff equation where $$K_i = \frac{IC_{50}}{1 + \frac{C}{Kd}}$$

wherein:
$K_i$ = inhibition constant.
C = concentration of [³H]-mesulergine
Kd = Affinity of mesulergine for 5-$HT_{1C}$ binding sites.
Curzon, G. A. and Kennett, G. A. (1990). TIPS, Vol. 11, 181-182. Fozard, J. R. and Gray, J. A. (1989). TIPS, Vol. 10, 307-309. Pazos, A. et al. (1984). Eur. J. Pharmacol., 106, 531-538.

Results are shown in Table 2.

TABLE 2

| Compound | [³]-Mesulergine $pK_i$ |
|---|---|
| E1 | 7.6 |
| E2 | 6.8 |
| E3 | 6.7 |
| E4 | 6.7 |
| E5 | 6.7 |
| E6 | 6.5 |

Compounds of the remaining examples have a $pK_i > 5$.

Rat stomach fundus

5-Hydroxytryptamine (5-HT) induces contractions of the rat stomach fundus through a 5-HT receptor that has the characteristics of a 5-$HT_{1C}$ receptor (Blackburn et al, 1990). Hence, this tissue can be used to assess the 5-$HT_{1C}$ antagonist actions of test drugs.

Rat stomach strips (6×4 mm) were suspended under a 4 g tension in 5 ml baths containing Tyrode solution, gassed with a mixture of 95% $O_2$/5% $CO_2$. After a 1 hour equilibration period, two dose response curves were constructed to 5-HT (final concentrations, $10^{-9}$ to $3\times10^{-6}$ M). Test drugs were then incubated at a final concentration of $10^{-6}$ M for 30 mins and another dose-response curve constructed to 5-HT. The apparent dissociation constant of a test drug, $K_B$, can be calculated from the equation where $$K_B = \frac{[B]}{DR - 1}$$

where B=concentration of the test drug and DR=the dose ratio (the factor by which the concentration of the agonist has to be increased in the presence of the test drug to obtain an identical effect observed in the absence of the test drug).

The results are shown in Table 3.

Blackburn et al. (1990). Eur. J. Pharmacol., 180, 229-237.

TABLE 3

| Compound | $K_B$ |
|---|---|
| E1 | $3.2 \times 10^{-8}$ M |
| E2 | $1 \times 10^{-7}$ M |
| E3 | $2.5 \times 10^{-8}$ M |
| E4 | $4.0 \times 10^{-7}$ M |
| E5 | $2.5 \times 10^{-7}$ M |
| E6 | $1.7 \times 10^{-7}$ M |

Social Interaction Test

Potential anxiolytic properties have been evaluated using the social interaction test based on that described by File (1980 J. Neurosci. Meth., 2, 219). Active social interaction between male rats is usually quantitated by counting interactive behaviours such as following, grooming, sniffing, climbing over or under, biting, mounting and boxing. This behaviour is supressed when the rats encounter each other in an environment which is novel and brightly lit. Under these circumstances anxiolytic drugs will enhance the level of social interaction.

Rats were housed in groups of 8 in a holding room adjacent to the experimental chamber for 8 days. They were then housed singly in the same room for 3 days prior to the experimental day. On the experimental day rats were injected p.o. 1 h pretest with vehicle or drug in pairs at 15 min intervals beginning at 10.00 am. 60 Mins later they were placed with a weight matched pair mate (encountered for the first time) in the social interaction box in a separate room. The box was made of while perspex 54×37×26 cm with no lid. The floor was divided into 24 equal squares and the cage was brightly lit. Active social interaction was scored blind over the next 15 min by remote video monitoring to give total interaction scores. The number of squares crossed by each rat was also scored and summed. At the end of each test the box was carefully wiped with a damp cloth. Unlike anxiolytic drugs, treatments that enhance social interaction by stimulant action will also increase locomotion. Treatments that are sedative reduce locomotion.

Test Results

The compound of Example 2 showed a significant increase in social interaction at doses of 2-40 mg/kg.

Geller-Seifter Procedure

Potential anxiolytic properties are evaluated using the Geller-Seifter procedure based on that originally described by Geller and Seifter, (1960) Psychopharmacologia, 1, 482-492. This procedure has been shown to be selective for drugs with anxiolytic properties (Cook and Sepinwall, (1975) "Mechanism of Action of Benzodiazepines" ed. Costa, E. and Greengard, P., Raven Press, New York, pp. 1-28).

Rats are trained on a variable interval 30 sec schedule (VI30) to press a lever in order to obtain food reward. The 5 min sessions of the VI30 schedule alternate with 2-5 min of a schedule (FR5) in which every 5th lever press is followed by presentation of a food pellet paired with a 0.5 sec mild footshock. The total study lasts approximately 30 mins. Rats typically respond with high rates of lever pressing under the VI30 schedule and low response rates under the FR5 'conflict' session. Anxiolytic drugs increase the suppressed response rates of rats in a 'conflict' session.

Drugs are administered intraperitoneally or orally to groups of 3-8 rats 30 min before testing.

The results are expressed as the percentage increase in the square root of the total number of lever presses in the FR5 'conflict' session. Square root transformation is necessary to normalise the data for statistical analysis using parametric methods.

The compound of Example 2 showed a significant increase in responding in the 'conflict' session at dose levels in the range 5-40 mg/kg p.o.

We claim:

1. A compound of Formula (I) or a pharmaceutically acceptable salt thereof:

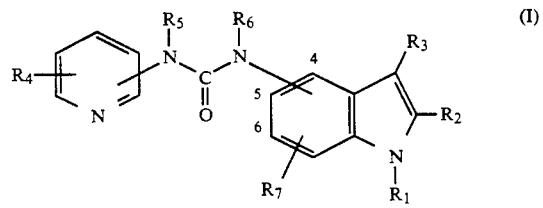

wherein:

$R_1$, $R_2$ and $R_3$ are independently hydrogen or $C_{1-6}$ alkyl;

$R_4$ is hydrogen, $C_{1-6}$ alkyl, halogen, hydroxy or $NR_8R_9$ where $R_8$ and $R_9$ are independently hydrogen or $C_{1-6}$ alkyl;

$R_5$ and $R_6$ are independently hydrogen or $C_{1-6}$ alkyl; and $R_7$ is hydrogen, $C_{1-6}$ alkyl or halogen; and wherein the urea moiety is attached at the 4-, 5- or 6-position of the indole ring.

2. A compound according to claim 1 wherein the urea moiety is attached at the 3-, 4- or 5-position of the pyridine ring.

3. A compound according to claim 1 wherein the urea moiety is attached at the 4-or 5-position of the indole ring.

4. A compound according to claim 1 wherein any alkyl moiety within variables $R_1$ to $R_9$ is $C_{1-3}$ alkyl.

5. A compound according to claim 1 wherein $R_1$ is methyl, $R_2$ is methyl or hydrogen, $R_3$ is hydrogen, methyl, ethyl, n-propyl or iso-propyl, $R_4$ is hydrogen and $R_5$, $R_6$ and $R_7$ are independently hydrogen or methyl.

6. A compound according to claim 1 selected from the group consisting of:
  N-(1,2-Dimethyl-3-ethyl-1H-indol-5-yl)-N'-(3-pyridyl)-urea,
  N-(1-Methyl-1H-indol-5-yl)-N'-(3-pyridyl)urea,
  N-(1,2,3-Trimethyl-1H-indol-5-yl)-N'-(3-pyridyl)urea,
  N-(1-Propyl-1H-indol-5-yl)-N'-(3-pyridyl)urea,
  N-(1-Methyl-1H-indol-4-yl)-N'-(3-pyridyl)urea,
  N-(1-Methyl-1H-indol-6-yl)-N'-(3-pyridyl)urea,
  N-(1H-Indol-5-yl)-N'-(3-pyridyl)urea,
  (1-Methyl-1H-indol-5-yl)-N'-methyl-N'-(3-pyridyl)urea,
  N-Methyl-N-(1-methyl-1H-indol-5-yl)-N'-(3-pyridyl)urea,
  N-Methyl-N-(1-methyl-1H-indol-5-yl)-N'-methyl-N'-(3-pyridyl)urea,
  N-(1-Methyl-1H-indol-5-yl-N'-(2-pyridyl)urea,
  N-(1,4-Dimethyl-1H-indol-5-yl)-N'-(3pyridyl)urea,
  N-(b 1-Methyl-1H-indol-5-yl)-N'-(2-chloropyrid-3-yl)urea,
  N-(1-Methyl-1H-indol-5-yl)-N'-(2-chloropyrid-5-yl)urea,
  N-(1-Methyl-1H-indol-5-yl)-N'-(3-hydroxypyrid-2-yl)urea,
  N-(1,3-Diethyl-2-methyl-1H-indol-5yl)-N'-(3-pyridyl)urea,
  N-(1,2-Dimethyl-3-propyl-1H-indol-5yl)-N'-(3-pyridyl)urea,
  N-(1,2-Dimethyl-3-n-hexyl-1H-indol-5yl)-N'-(3-pyridyl)urea,
  N-(1-Methyl-1H-indol-4-yl)-N'-(4-pyridyl)urea,
  N-(3-Ethyl-1-methyl-1H-indol-5-yl)-N'-(3-pyridyl)urea,
  N-(1,2-Dimethyl-3-ethyl-1H-indol-5-yl)-N'-(2-pyridyl)urea,
  N-(1,2-Dimethyl-3-ethyl-1H-indol-5-yl)-N'-(4-pyridyl)urea,
  N-(1-Methyl-1H-indol-5-yl)-N'-(2-dimethylamino-5-pyridyl)urea,
  N-(1,2-Dimethyl-3-isopropyl-1H-indol-5-yl)-N'-(3-pyridyl)urea,
  N-(1,3-Diethyl-1H-indol-5-yl)-N'-(3-pyridyl)urea,
  N-(3-Isopropyl-1-methyl-1H-indol-5-yl)-N'-(3-pyridyl)urea, or
  N-(1,3-Dimethyl-1H-indol-5-yl)-N'-(3-pyridyl)urea;
  or pharmaceutically acceptable salts thereof.

7. A pharmaceutical composition which comprises an effective amount of a compound according to claim 1 and a pharmaceutically acceptable carrier.

8. A method of treatment or prophylaxis of anxiety, depression in mammals including humans, which comprises administering to the subject in need thereof, a therapeutically effective amount of a compound according to claim 1.

* * * * *